(12) United States Patent
Sugimoto et al.

(10) Patent No.: US 9,228,944 B2
(45) Date of Patent: *Jan. 5, 2016

(54) SAMPLE ANALYSIS ELEMENT AND DETECTION DEVICE

(71) Applicant: SEIKO EPSON CORPORATION, Tokyo (JP)

(72) Inventors: Mamoru Sugimoto, Chino (JP); Jun Amako, Shiki (JP); Hideaki Nishida, Chino (JP)

(73) Assignee: Seiko Epson Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/395,243

(22) PCT Filed: Apr. 12, 2013

(86) PCT No.: PCT/JP2013/002503
§ 371 (c)(1),
(2) Date: Oct. 17, 2014

(87) PCT Pub. No.: WO2013/157233
PCT Pub. Date: Oct. 24, 2013

(65) Prior Publication Data
US 2015/0103347 A1 Apr. 16, 2015

(30) Foreign Application Priority Data
Apr. 18, 2012 (JP) ................. 2012-094519

(51) Int. Cl.
*G01N 21/55* (2014.01)
*G01N 21/552* (2014.01)
*G01N 21/65* (2006.01)

(52) U.S. Cl.
CPC ............ *G01N 21/553* (2013.01); *G01N 21/658* (2013.01); *G01N 2201/06113* (2013.01)

(58) Field of Classification Search
CPC ... G01N 21/553; G01N 21/55; G01N 21/554; G01N 21/474; G01N 21/57
USPC ........................................................ 356/445
See application file for complete search history.

(56) References Cited

U.S. PATENT DOCUMENTS 7,079,250 B2 7/2006 Mukai
7,088,449 B1 8/2006 Brongersma
(Continued)

FOREIGN PATENT DOCUMENTS

EP 2372348 A1 10/2011
JP 2000-356587 A 12/2000
(Continued)

OTHER PUBLICATIONS

Chu, Yizhuo et al., "Double resonance surface enhanced Raman scattering substrates: an intuitive coupled oscillator model", Optics Express, Aug. 1, 2011, pp. 14919-14928, vol. 19, No. 16, USA.

(Continued)

*Primary Examiner* — Tarifur Chowdhury
*Assistant Examiner* — Md Rahman
(74) *Attorney, Agent, or Firm* — Harness, Dickey & Pierce, P.L.C.

(57) ABSTRACT

There is provided a sample analysis element capable of uniting a propagating surface plasmon resonance with a localized surface plasmon resonance while increasing the surface density of the hot spots. The sample analysis element is provided with a plurality of metal nanobody lines. Each of the metal nanobody lines includes a plurality of metal nanobodies arranged in a line on a dielectric surface at a first pitch smaller than a wavelength of incident light, and the plurality of metal nanobody lines is arranged in parallel to each other at a second pitch larger than the first pitch.

7 Claims, 11 Drawing Sheets

(56) References Cited

U.S. PATENT DOCUMENTS

| | | |
|---|---|---|
| 7,351,588 B2 | 4/2008 | Poponin |
| 7,399,445 B2 | 7/2008 | Kuroda et al. |
| 7,483,130 B2 | 1/2009 | Baumberg et al. |
| 7,639,355 B2 | 12/2009 | Fattal et al. |
| 7,733,491 B2 | 6/2010 | Kuroda et al. |
| 7,768,640 B2 | 8/2010 | Cunningham et al. |
| 8,085,405 B2 | 12/2011 | Ogawa |
| 8,093,065 B2 | 1/2012 | Poponin |
| 8,107,071 B2 | 1/2012 | Kimura |
| 8,247,216 B2 | 8/2012 | Zaccarin et al. |
| 2004/0183176 A1 | 9/2004 | Naya et al. |
| 2005/0067935 A1* | 3/2005 | Lee et al. .............. 313/309 |
| 2006/0194344 A1 | 8/2006 | Saito |
| 2007/0090411 A1 | 4/2007 | Naya et al. |
| 2008/0198376 A1 | 8/2008 | Poponin |
| 2009/0002701 A1 | 1/2009 | Fattal et al. |
| 2009/0109422 A1 | 4/2009 | Handa et al. |
| 2010/0167946 A1 | 7/2010 | Shaw et al. |
| 2010/0178713 A1 | 7/2010 | Nishiuma et al. |
| 2010/0233825 A1 | 9/2010 | Yamada et al. |
| 2010/0309539 A1* | 12/2010 | Kaye et al. .............. 359/288 |
| 2011/0114859 A1 | 5/2011 | Amako et al. |
| 2011/0116088 A1 | 5/2011 | Amako et al. |
| 2011/0164252 A1 | 7/2011 | Handa et al. |
| 2012/0019828 A1 | 1/2012 | McCaffrey et al. |
| 2012/0107958 A1 | 5/2012 | Poponin |
| 2012/0257204 A1 | 10/2012 | Walters |

FOREIGN PATENT DOCUMENTS

| | | |
|---|---|---|
| JP | 2003-268592 A | 9/2003 |
| JP | 2003-270132 A | 9/2003 |
| JP | 2004-279364 A | 10/2004 |
| JP | 2006-003149 A | 1/2006 |
| JP | 2006-208057 A | 8/2006 |
| JP | 2007-218900 A | 8/2007 |
| JP | 2007-240361 A | 9/2007 |
| JP | 2007-248284 A | 9/2007 |
| JP | 2007-303973 A | 11/2007 |
| JP | 2008-025989 A | 2/2008 |
| JP | 2008-292425 A | 12/2008 |
| JP | 2009-085724 A | 4/2009 |
| JP | 2009-115492 A | 5/2009 |
| JP | 2009-222401 A | 10/2009 |
| JP | 2010-020136 A | 1/2010 |
| JP | 2010-531995 A | 9/2010 |
| JP | 2010-256161 A | 11/2010 |
| JP | 2011-128133 A | 6/2011 |
| JP | 2011-128135 A | 6/2011 |
| JP | 2011-141264 A | 7/2011 |
| JP | 2011-141265 A | 7/2011 |
| WO | WO-2009-002524 A2 | 12/2008 |
| WO | WO-2013-058739 A1 | 4/2013 |

OTHER PUBLICATIONS

Chu, Yizhuo and Crozier, Kenneth B., "Experimental study of the interaction between localized and propagating surface plasmons", Optics Letters, Feb. 1, 2009, pp. 244-246, vol. 34, No. 3, USA.

Jean Cesario, "Electromagnetic Coupling Between a Metal Nanoparticle Grating and a Metallic Surface", Optical Society of America, Optics Letters, vol. 30, No. 24, Dec. 15, 2005, pp. 3404-3406.

N. Felidj et al., "Enhanced Substrate-Induced Coupling in Two-Dimensional Gold Nanoparticle Arrays", Physical Review B 66, The American Physical Society, 2002, pp. 245407-1 through 245407-7.

L. Du et al., "Localized Surface Plasmons, Surface Plasmon Polaritons, and Their Coupling in 2D Metallic Array for SERS", Optical Society of America, Optics Express, vol. 18, No. 3, Feb. 1, 2010, pp. 1959-1965.

M. Inoue et al., "Surface Enhanced Raman Scattering by Metal Spheres, I. Cluster Effect", Journal of the Physical Society of Japan, vol. 52, No. 11, Nov. 1983, pp. 3853-3864.

Extended European Search Report for Application No. EP 13 77 7779 dated Oct. 20, 2015 (7 pages).

* cited by examiner

SAMPLE ANALYSIS ELEMENT AND DETECTION DEVICE

CROSS-REFERENCE TO RELATED APPLICATIONS

This application is a U.S. National Phase Application of PCT/JP2013/002503, filed on Apr. 12, 2013, and published in Japanese as WO 2013/157233 A1 on Oct. 24, 2013. This application claims priority to Japanese Application No. 2012-094519, filed on Apr. 18, 2012. The entire disclosures of the above applications are incorporated herein by reference.

TECHNICAL FIELD

The invention relates to a sample analysis element provided with metal nanobodies such as metal nanoparticles or metal nano-projections, and a detection device or the like using such a sample analysis element.

BACKGROUND ART

There is known a sample analysis element using localized surface plasmon resonance (LSPR). Such a sample analysis element is provided with, for example, metal nanobodies distributed on a dielectric surface, namely a metal nanostructure. The metal nanostructure is formed to be sufficiently smaller than the wavelength of excitation light, for example. When the metal nanoparticles are irradiated with the excitation light, all electrical dipoles are aligned, and thus an enhanced electrical field is induced. As a result, near-field light is generated on the surface of the metal nanostructure. So-called hot spots are formed.

In Yizhuo Chu et al., "Experimental study of the interaction between localized and propagating surface plasmons," OPTICS LETTERS, U.S., Feb. 1, 2009, Vol. 34, No. 3, pp. 244-246, the metal nanostructure is arranged at a predetermined pitch forming a grid pattern. If the dimension of the pitch is set to a specific numerical value, a propagating surface plasmon resonance (PSPR) is caused based on an evanescent wave. The propagating surface plasmon resonance unites with the localized surface plasmon resonance. A so-called hybrid mode is established. In such a manner as described above, the localized surface plasmon resonance is enhanced by the propagating surface plasmon resonance, and thus, the near-field light is enhanced on the surface of the metal nanostructure.

SUMMARY OF INVENTION

Technical Problem

The sample analysis element can be used for a detection device of a target substance. As disclosed in Yizhuo Chu et al., if the pitch is set at the wavelength of the evanescent wave causing the propagating surface plasmon resonance, the surface density of the hot spots is remarkably lowered on the dielectric surface, and it is hard for the target substance to adhere to the hot spots.

According to at least one of the aspects of the invention, it is possible to provide the sample analysis element capable of uniting the localized surface plasmon resonance with the propagating surface plasmon resonance while increasing the surface density of the hot spots.

Solution to Problem (1) An aspect of the invention relates to a sample analysis element including a plurality of metal nanobody lines disposed on a dielectric surface, each of the metal nanobody lines including a plurality of metal nanobodies arranged in a line at a first pitch smaller than a wavelength of incident light, and the metal nanobody lines are arranged in parallel to each other at a second pitch larger than the first pitch.

The localized surface plasmon resonance is caused in the metal nanobodies by action of the incident light. By action of the pitch (the second pitch) of the metal nanobody lines, the propagating surface plasmon resonance is caused based on the evanescent wave. The propagating surface plasmon resonance unites with the localized surface plasmon resonance. A so-called hybrid mode is established. In such a manner as described above, the localized surface plasmon resonance is enhanced by the propagating surface plasmon resonance, and thus, the near-field light is enhanced on the surfaces of the metal nanobodies. So-called hot spots are formed. Moreover, since the plurality of metal nanobodies is disposed in each of the metal nanobody lines, the surface density of the metal nanobodies is increased compared to the case in which the metal nanobodies are arranged at the pitch of resonating with the incident light. Therefore, the surface density of the hot spots is increased.

(2) A region including no metal nanobody is formed between the metal nanobody lines. Specifically, in a space separated by the dielectric surface and an imaginary plane parallel to the dielectric surface and having contact with the top surfaces of the metal nanobodies, a space between the metal nanobody lines adjacent to each other is filled with an insulating body (including a space). In other words, the metal material is excluded from the space between the metal nanobody lines adjacent to each other in that space.

(3) The sample analysis element can be provided with a metal film, and a dielectric body extending on a surface of the metal film to form the dielectric surface. If the dipoles face to the same direction between the metal of the metal film and the metal of the metal nanobodies, the localized electrical field resonance is caused, and the near-field light is enhanced on the surfaces of the metal nanobodies. Similarly, if the dipoles face to directions opposite to each other between the metal of the metal film and the metal of the metal nanobodies, the localized electrical field resonance is caused, and the near-field light is enhanced on the surfaces of the metal nanobodies.

(4) The second pitch can be set to a dimension for establishing a first-order minimum of reflectance at a wavelength shorter than a resonance wavelength of a localized surface plasmon resonance generated in the metal nanobodies, and further establishing a higher-order minimum than the first-order at a wavelength longer than the resonance wavelength of the localized surface plasmon resonance. If the second pitch is set as described above, the reflectance is significantly reduced at a specific wavelength. As a result, the propagating surface plasmon surely unites with the localized surface plasmon. The near-field light is surely enhanced on the surfaces of the metal nanobodies.

(5) Such a sample analysis element as described above can be used while being incorporated in a detection device. The detection device can include the sample analysis element, a light source adapted to emit light toward the metal nanobody lines, and a light detector adapted to detect light emitted from the metal nanobody lines in accordance with irradiation with the light.

DESCRIPTION OF EMBODIMENT

Hereinafter, an embodiment of the invention will be explained with reference to the accompanying drawings. It should be noted that the present embodiment explained below does not unreasonably limit the content of the invention as set forth in the appended claims, and all of the constituents explained in the present embodiment are not necessarily essential as means for solving the problem according to the invention.

(1) Structure of Sample Analysis Element

Figure 1:
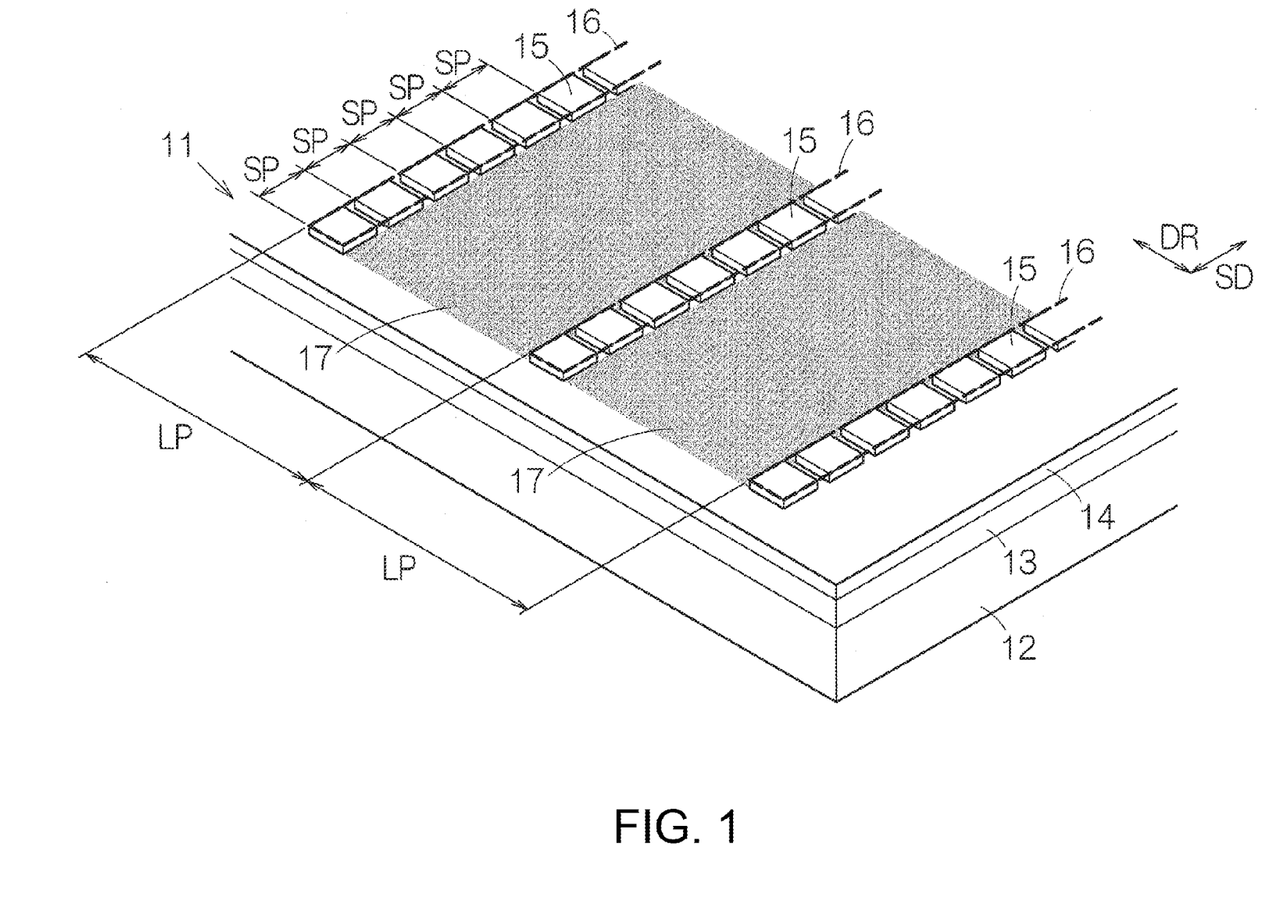
FIG. 1 is a perspective view schematically showing a sample analysis element according to an embodiment of the invention.

FIG. 1 schematically shows a sample analysis element 11 according to an embodiment of the invention. The sample analysis element 11 is provided with a substrate 12. The substrate 12 is formed of, for example, a dielectric body. As the dielectric body, glass can be used for example.

On the surface of the substrate 12, there is formed a metal film 13. The metal film 13 is formed of metal. The metal film 13 can be formed of, for example, gold. The metal film 13 is formed on, for example, the entire surface of the substrate 12 continuously. The film thickness of the metal film 13 can be set to a value equal to or larger than, for example, about 100 nm.

On the surface of the metal film 13, there is formed a dielectric film (dielectric body) 14. The dielectric film 14 is formed of a dielectric body. The dielectric film 14 can be formed of an oxide film such as silicon dioxide ($SiO_2$). The dielectric film 14 is formed on, for example, the entire surface of the metal film 13 continuously. The film thickness of the dielectric film 14 can be set to about 40 nm.

On the surface of the dielectric film 14, there are formed metal nano-projections (metal nanobodies) 15. The metal nano-projections 15 are distributed on the surface of the dielectric film 14. The metal nano-projections 15 are formed of metal. The metal nano-projections 15 can be formed of, for example, silver. Besides the above, in forming the metal nano-projections 15, gold or aluminum can also be used. Each of the metal nano-projections 15 is formed to be a prism. The horizontal cross-sectional surface of the prism is formed to be, for example, a square. The length of a side of the square can be set to, for example, about 1 through 1000 nm. The height (from the surface of the dielectric film) of the prism can be set to, for example, about 10 through 100 nm. The horizontal cross-sectional surface of the prism can be formed to be a polygon other than a square. The metal nano-projections 15 can also be formed to be a three-dimensional shape such as a cylinder.

The metal nano-projections 15 form metal nano-projection lines (metal nanobody lines) 16. In each of the metal nano-projection lines 16, the metal nano-projections 15 are arranged in a line on the surface of the dielectric surface 14 at a short pitch SP (a first pitch). The metal nano-projection lines 16 extend in a first direction SD. The short pitch SP is set to be smaller than the wavelength of the incident light.

The metal nano-projection lines 16 are arranged in parallel at a long pitch LP (a second pitch) in a second direction DR intersecting with the first direction SD. Here, the second direction DR is perpendicular to the first direction SD in an imaginary plane including the surface of the dielectric film 14. The long pitch LP is set to be larger than at least the short pitch SP. Preferably, the long pitch LP is set to be roughly equal to a peak wavelength of the localized plasmon resonance generated at the short pitch SP. As described later, the dimension of the long pitch LP is set in accordance with the wave number of the evanescent wave.

Between the metal nano-projection lines 16, there are formed nonmetallic regions (regions not including the metal nanobody) 17 not including the metal nano-projection. Specifically, in a space sandwiched by an imaginary plane including bottom surfaces of the metal nano-projections 15 and an imaginary plane including top surfaces of the metal nano-projections 15, a space between the metal nano-projection lines 16 adjacent to each other is filled with an insulating body (including a space). In other words, the metal material is excluded from the space between the metal nano-projection lines 16 adjacent to each other in that space. Here, the surface of the dielectric film 14 is exposed in the space between the metal nano-projection lines 16.

In the sample analysis element 11, the size of each of the metal nano-projections 15 is set to be sufficiently smaller than the wavelength of the incident light. As a result, the localized surface plasmon resonance (LSPR) is caused in the metal nano-projections 15 by action of the incident light. In addition, if the polarization plane of the incident light is adjusted to the second direction DR, the propagating surface plasmon resonance (PSPR) is caused based on the evanescent wave in accordance with the setting of the long pitch LP. The propagating surface plasmon resonance unites with the localized surface plasmon resonance in the metal nano-projections 15. A so-called hybrid mode is established. In such a manner as described above, the localized surface plasmon resonance is enhanced by the propagating surface plasmon resonance, and thus, the near-field light is enhanced on the surfaces of the metal nano-projections 15. So-called hot spots are formed. Moreover, since the pitch of the metal nano-projections 15 is set to the short pitch SP smaller than the long pitch LP in each of the metal nano-projection lines 16, the surface density of the metal nano-projections 15 is increased compared to the case in which the pitch of the metal nano-projections 15 is set to the long pitch LP. The surface density of the hot spots is increased.

In this sample analysis element 11, the long pitch LP is set to a dimension for establishing a first-order minimum of the reflectance at a wavelength shorter than the resonance wavelength of the localized surface plasmon resonance generated in the metal nano-projections 15 and further establishing higher-order minimums than the first order at a wavelength longer than the resonance wavelength of the localized resonance plasmon resonance. If the long pitch LP is set as described above, the reflectance is significantly reduced at a specific wavelength. As a result, the propagating surface plasmon surely unites with the localized surface plasmon. The near-field light is surely enhanced on the surfaces of the metal nano-projections 15.

(2) Verification of Electrical Field Intensity

Figure 2A:
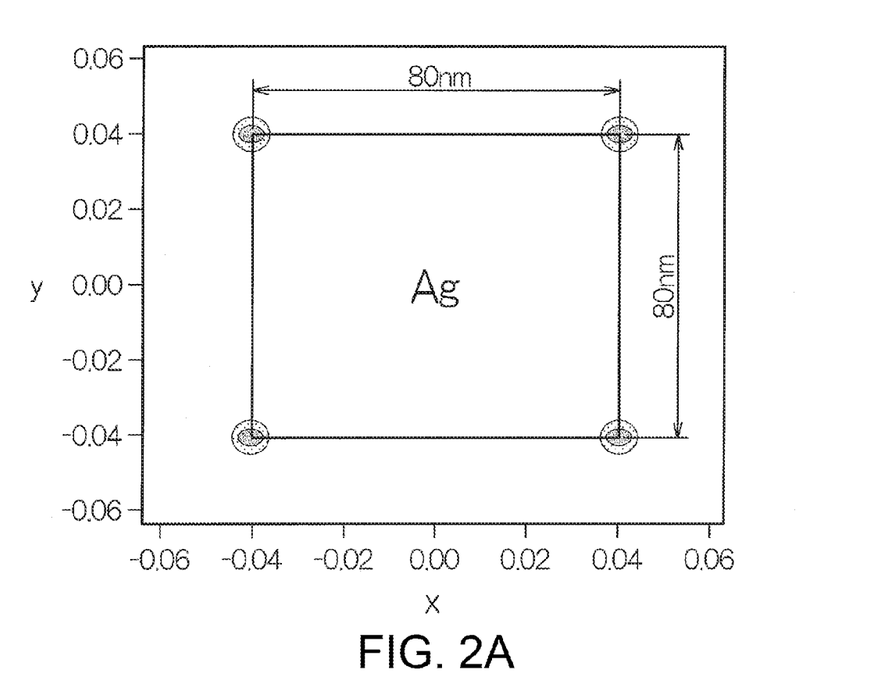
FIGS. 2(a) and 2(b) are a plan view and a side view, respectively, showing a unit of a simulation model.
Figure 2B:
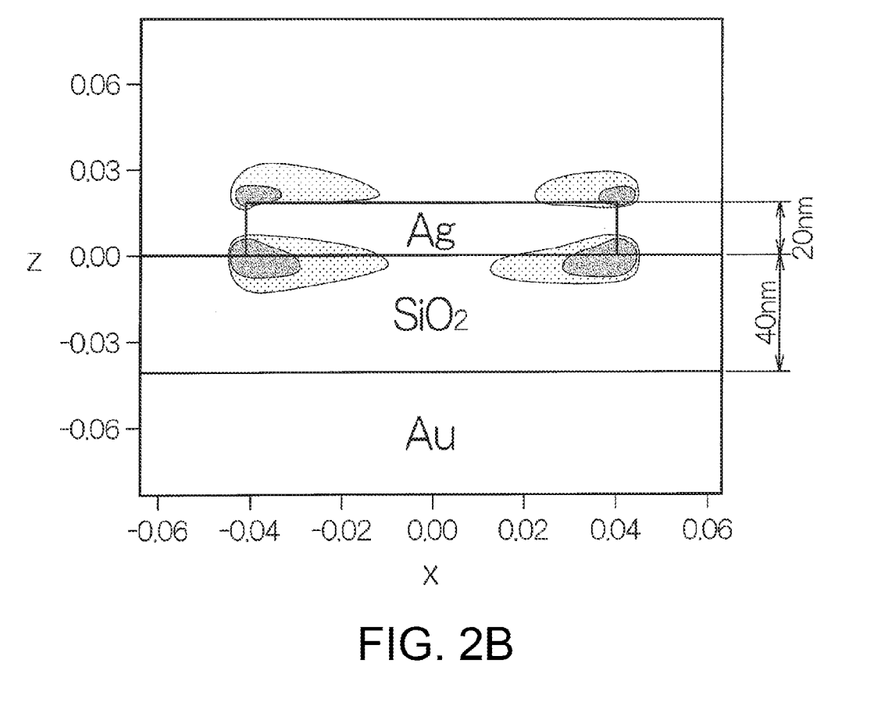

The inventors verified the electrical field intensity of the sample analysis element 11. In the verification, simulation software of Finite-Difference Time-Domain (FDTD) method is used. As shown in FIG. 2(a) and FIG. 2(b), the inventors built a unit of a simulation model based on Yee Cell. In the unit, there was formed the metal film 13, 120 nm on a side. To the metal film 13, gold was set. On the metal film 13, there was formed the dielectric film 14. To the dielectric film 14, silicon dioxide ($SiO_2$) was set. The film thickness of the dielectric film 14 was set to 40 nm. On the dielectric film 14, there was formed the metal nano-projection 15, 80 nm on a side. To the metal nano-projection 15, silver was set. The height (from the surface of the dielectric film 14) of the metal nano-projection 15 was set to 20 nm.

Figure 3A:
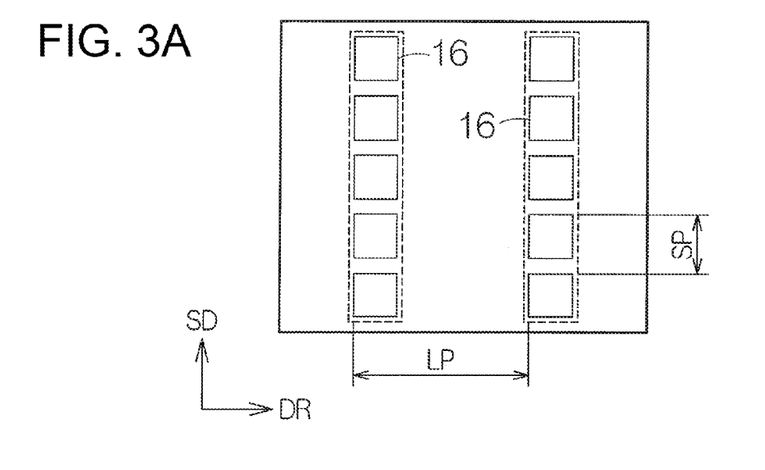
FIGS. 3(a), 3(b) and 3(c) are plan views of a model according to the present embodiment, a first comparison model, and a second comparison model, respectively, of the simulation model.

As shown in FIG. 3(a), a single metal nano-projection line 16 was formed by a line of units, namely the metal nano-projections 15. A plurality of metal nano-projection lines 16 were arranged in parallel to each other. The long pitch LP was set in an x-axis direction between the metal nano-projection lines 16. In the first through seventh models, the long pitch LP was set to 240 nm, 360 nm, 480 nm, 550 nm, 600 nm, 720 nm, and 840 nm, respectively. As a result, between the metal nano-projection lines 16, there was formed the nonmetallic region 17 with a line of void units. The void unit was formed of a void, 120 nm on a side. The electrical field intensity Ex was calculated in the leading metal nano-projection 15. There was set "peripheral refractive index ns=1." The incident light as linearly polarized light was set. The polarization plane was adjusted to the x-axis direction. The incident light was set to normal incidence. In the metal nano-projection 15, the electrical field was concentrated along a ridge line perpendicular to the surface of the dielectric film 14.

Figure 3B:
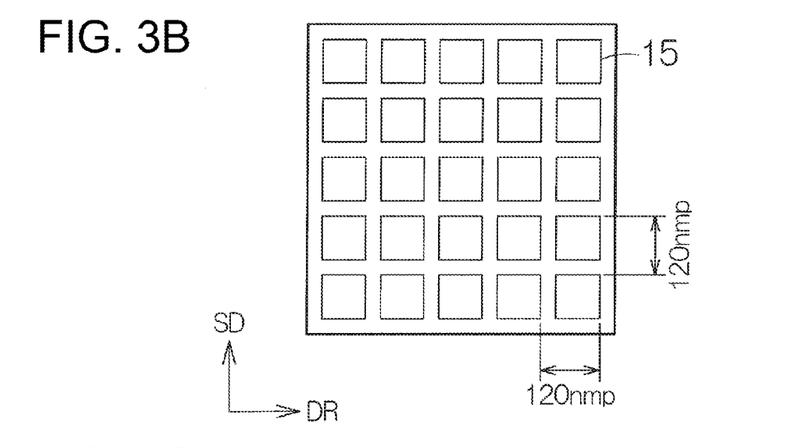
Figure 3C:
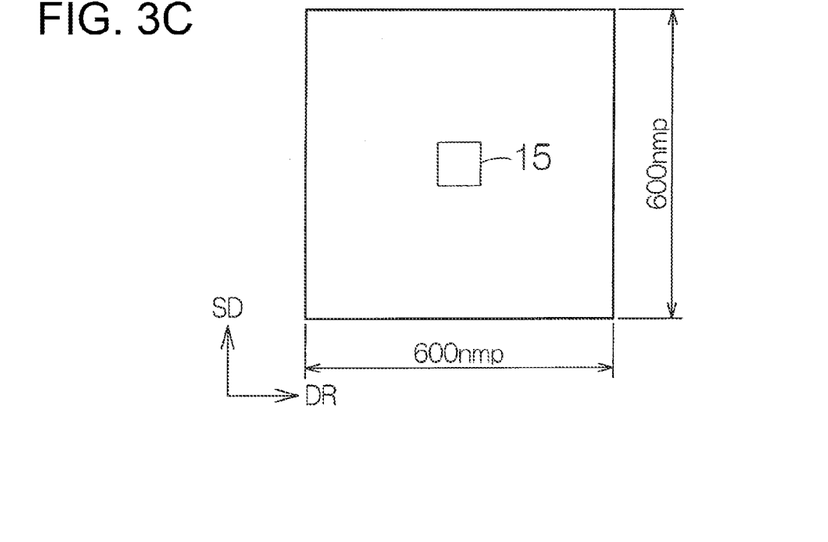

As shown in FIG. 3(b), the inventors prepared a first comparative model. In the first comparative model, the nonmetallic regions 17 were eliminated. In other words, the metal nano-projection lines 16 were not set. Simply, the metal nano-projections 15 were arranged in a grid pattern at the short pitch SP. Similarly to the above, the electrical field intensity Ex was calculated in selected one of the metal nano-projections 15. Similarly, as shown in FIG. 3(c), the inventors prepared a second comparative model. In the second comparative model, a pitch of 600 nm was set between the metal nano-projections 15 in each of the first direction DR and the second direction SD.

Figure 4:
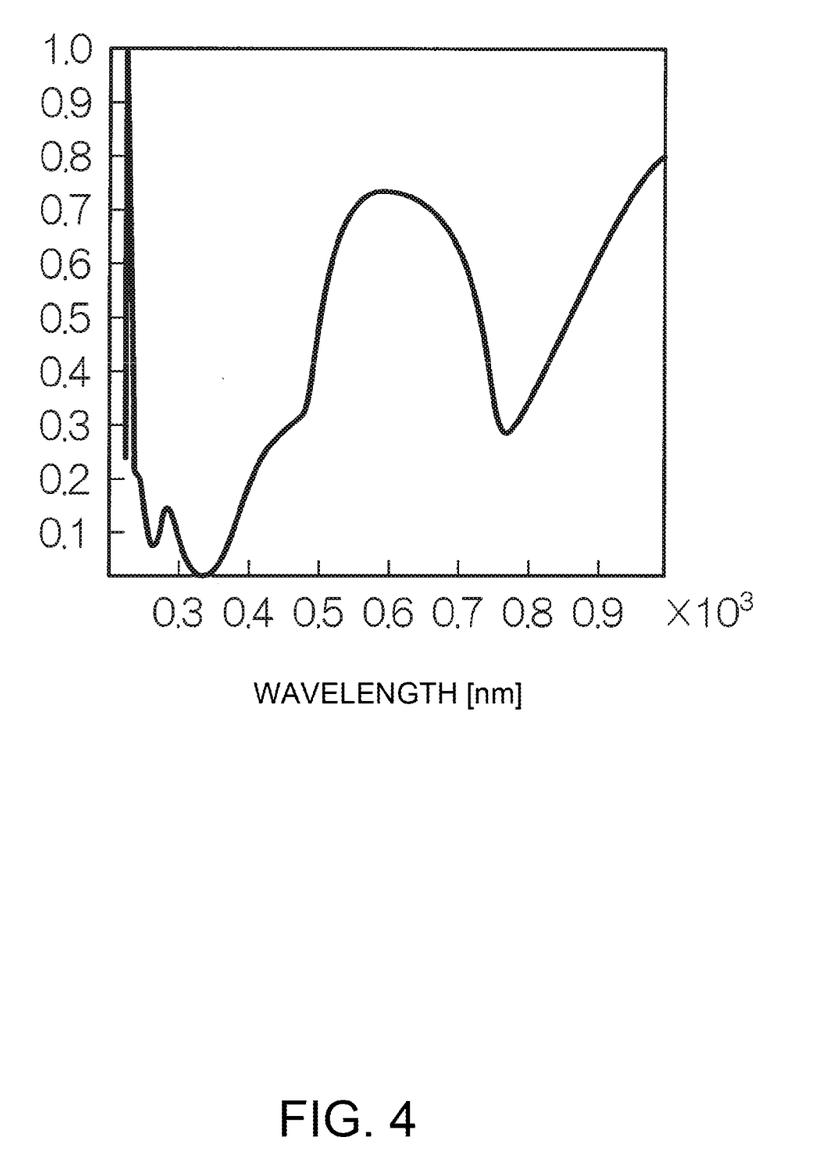
FIG. 4 is a graph showing a wavelength dependency of the reflectance of the first comparative model.
Figure 5:
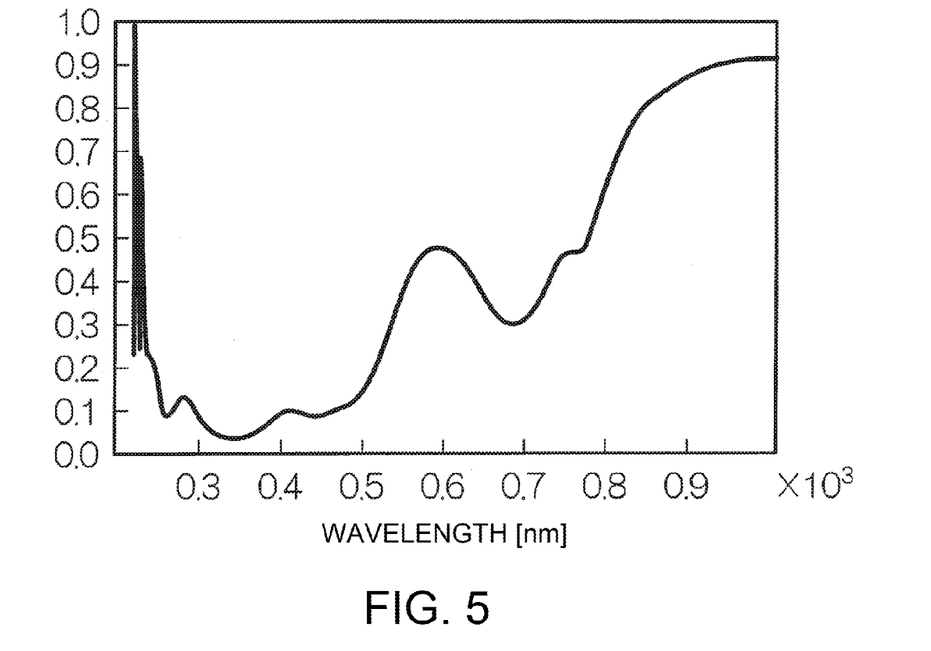
FIG. 5 is a graph showing a wavelength dependency of the reflectance of a first model.
Figure 6:
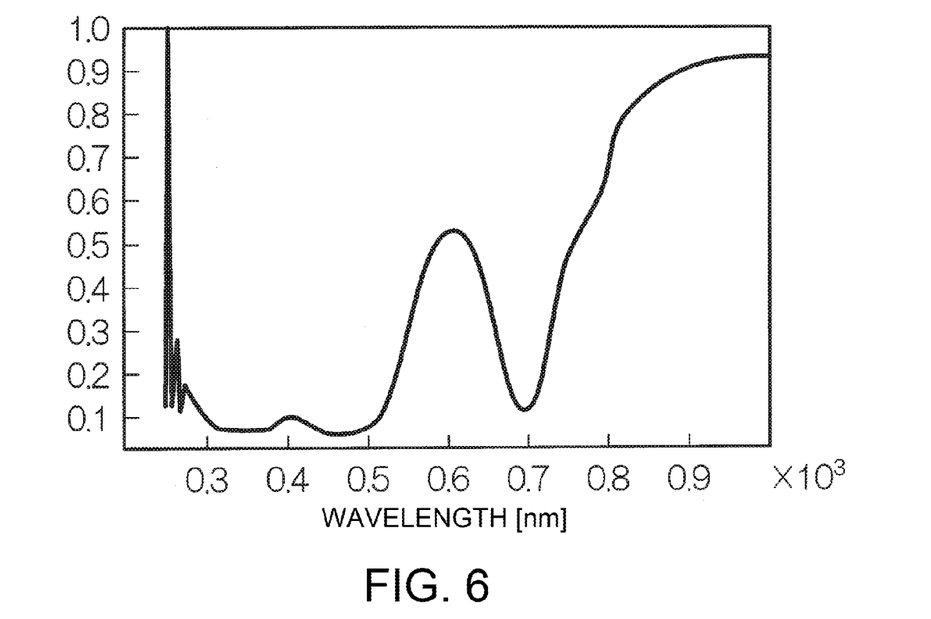
FIG. 6 is a graph showing a wavelength dependency of the reflectance of a second model.
Figure 7:
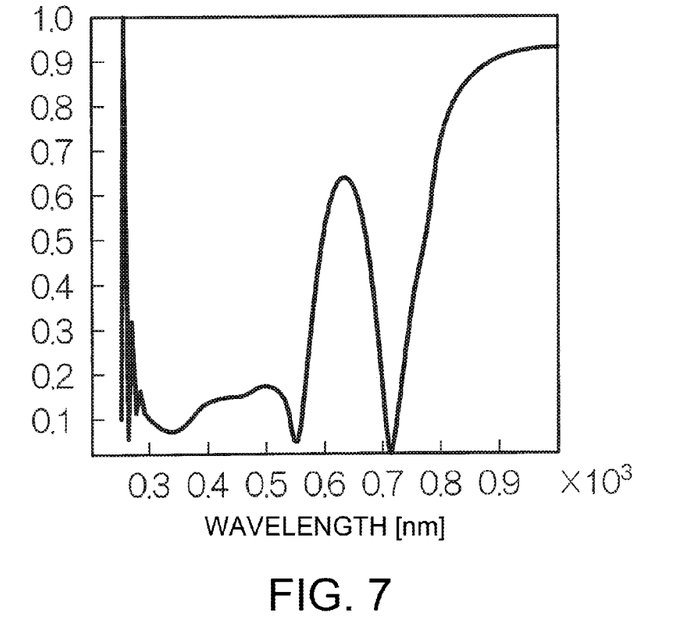
FIG. 7 is a graph showing a wavelength dependency of the reflectance of a third model.
Figure 8:
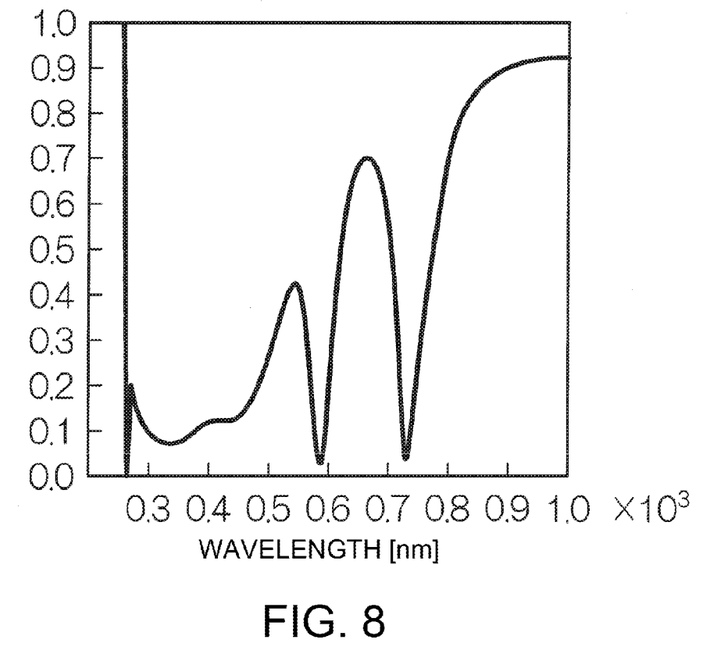
FIG. 8 is a graph showing a wavelength dependency of the reflectance of a fourth model.
Figure 9:
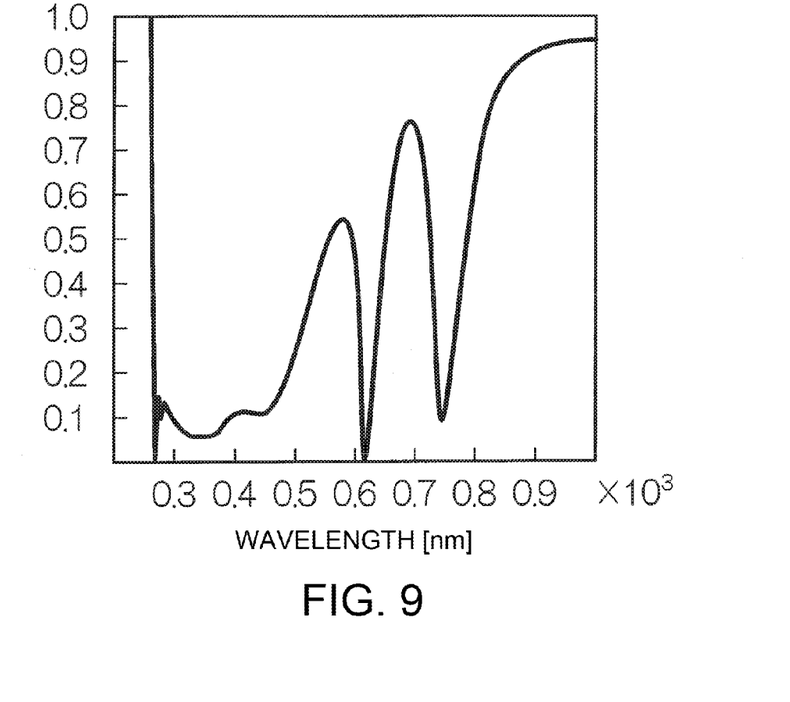
FIG. 9 is a graph showing a wavelength dependency of the reflectance of a fifth model.
Figure 10:
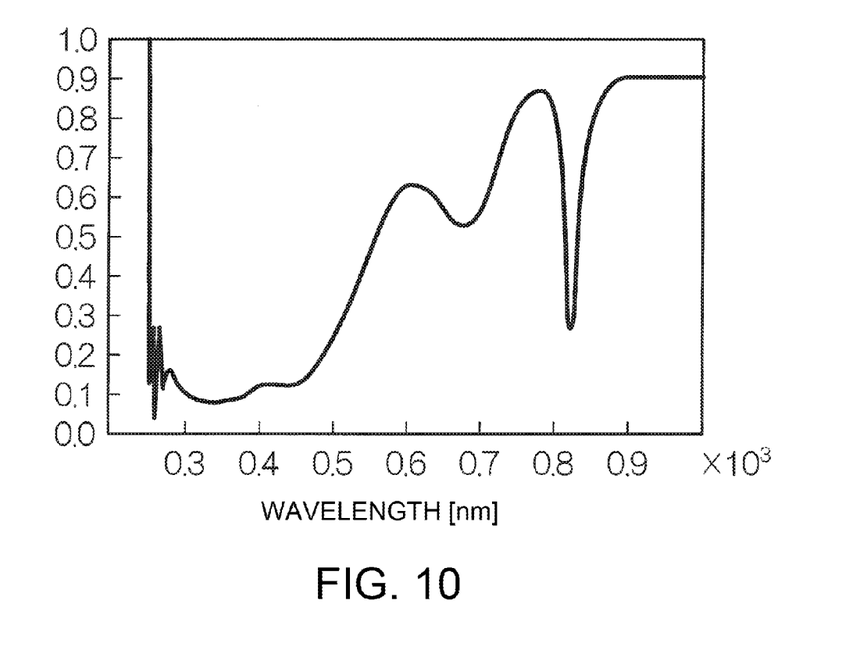
FIG. 10 is a graph showing a wavelength dependency of the reflectance of a sixth model.
Figure 11:
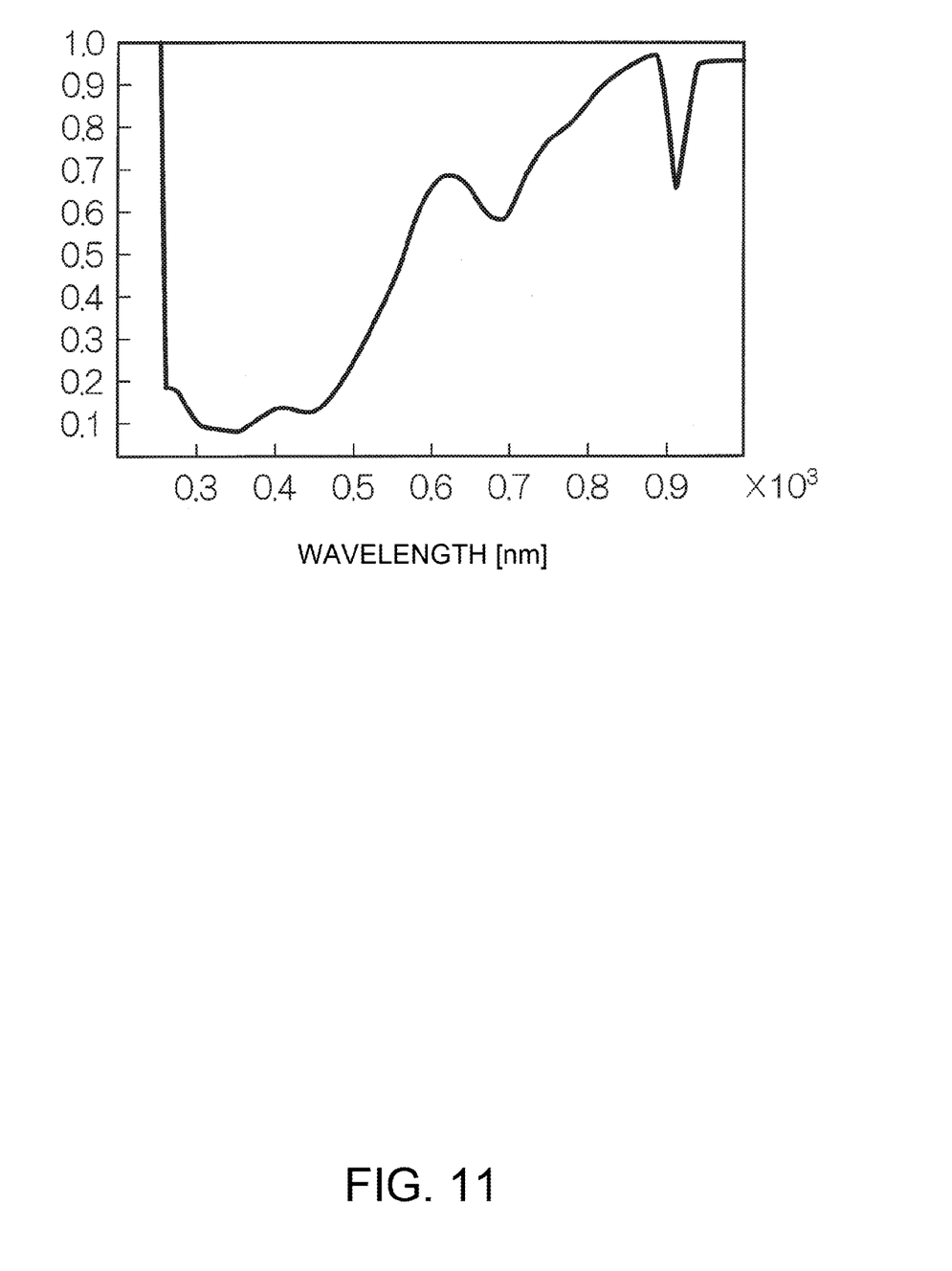
FIG. 11 is a graph showing a wavelength dependency of the reflectance of a seventh model.

FIG. 4 shows a wavelength dependency of the reflectance of the first comparative model. FIGS. 5 through 11 show wavelength dependencies of the reflectance of the first through seventh models. In the case in which a localized electrical field resonance occurs, a drop of the reflectance is observed. It is conceivable that the dipoles face to the same direction in gold (Au) and silver (Ag) at the minimum (corresponding to the first-order minimum) appearing at a high frequency, and it is conceivable that the dipoles of gold (Au) and silver (Ag) face to opposite directions at the minimum (corresponding to the high-order minimum higher than the first order) appearing at a frequency lower than that of the first-order minimum. As shown in FIGS. 5 and 6, in the first model and the second model, the second-order minimum was observed around the wavelengths of 683 nm and 696 nm, respectively. As shown in FIGS. 7 through 9, in the third through fifth models, the first-order minimum was observed at the wavelengths of 555 nm, 590 nm, and 620 nm, respectively, and the second-order minimum was observed at the wavelengths of 715 nm, 730 nm, and 745 nm, respectively. In the third model, the reflectance stood at roughly "0 (zero)" at the wavelength of 715 nm. In the fourth model, the reflectance approached roughly "0" at the wavelengths of 590 nm and 730 nm. In the fifth model, the reflectance stood at roughly "0" at the wavelength of 620 nm.

Figure 12:
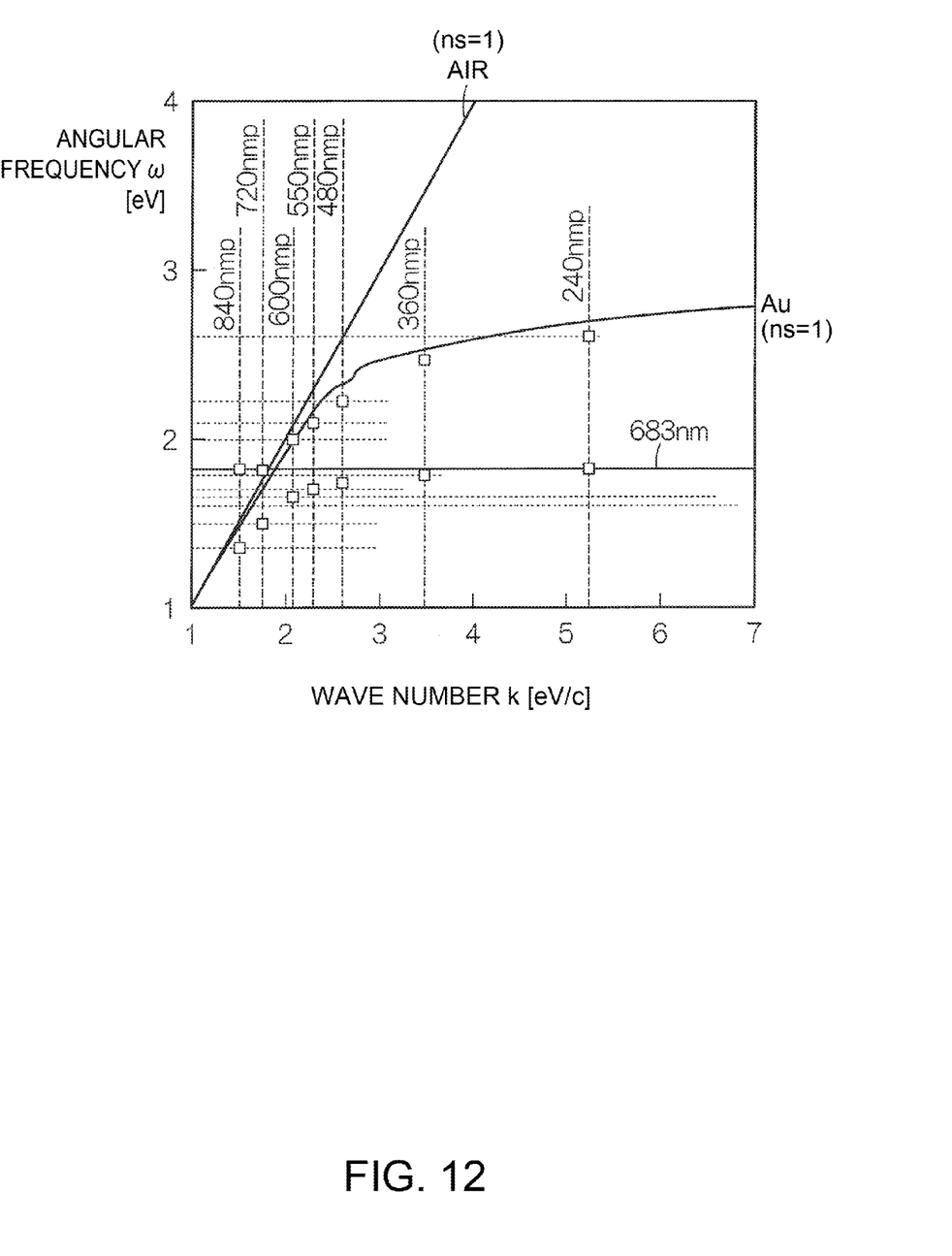
FIG. 12 is a graph showing a distribution relationship formed based on minimums of the reflectance shown in FIGS. 5 through 11.

FIG. 12 shows a distribution relationship formed from the minimums of the reflectance in the respective models. The wavelength (=683 nm) appearing in common to the plurality of long pitches LP corresponds to the resonance wavelength of the localized surface plasmon resonance. This is because the gradient of the distribution relationship represents the moving speed of the propagating plasmon, the gradient of the angular frequency showing the high-order minimum in the first model (LP=240 nm) stands at 0 (zero), and similarly, the gradient of the angular frequency showing the first-order minimum in the sixth model (LP=720 nm) and the seventh model (LP=840 nm) stands at 0 (zero). The resonance wavelength of the localized surface plasmon resonance can be determined in accordance with the volume of the metal nano-projections 15 and the film thickness of the dielectric film 14. Further, it is conceivable that the wavelength showing the minimum of the reflectance other than the resonance wavelength (=683 nm) of the localized surface plasmon for each of the long pitches LP is mainly the propagating surface plasmon. This is a result of the fact that the interaction between the metal nano-projections 15 increases as the lines of the metal nano-projections 15 per unit area increase, and thus the red-shift, namely the shift toward the long wavelength side, of the resonance wavelength occurs. The shift toward the long wavelength side, or the red-shift of the resonance peak wavelength represents the strength of the interaction between the metal nano-projections 15. The Anti-Crossing Behavior (known as an index of the hybrid mode) was observed similarly to Yizhuo Chu et al., based on the wavelength of 683 nm and the distribution relationship curve of the propagating surface plasmon resonance of gold Au (ns=1).

Figure 13:
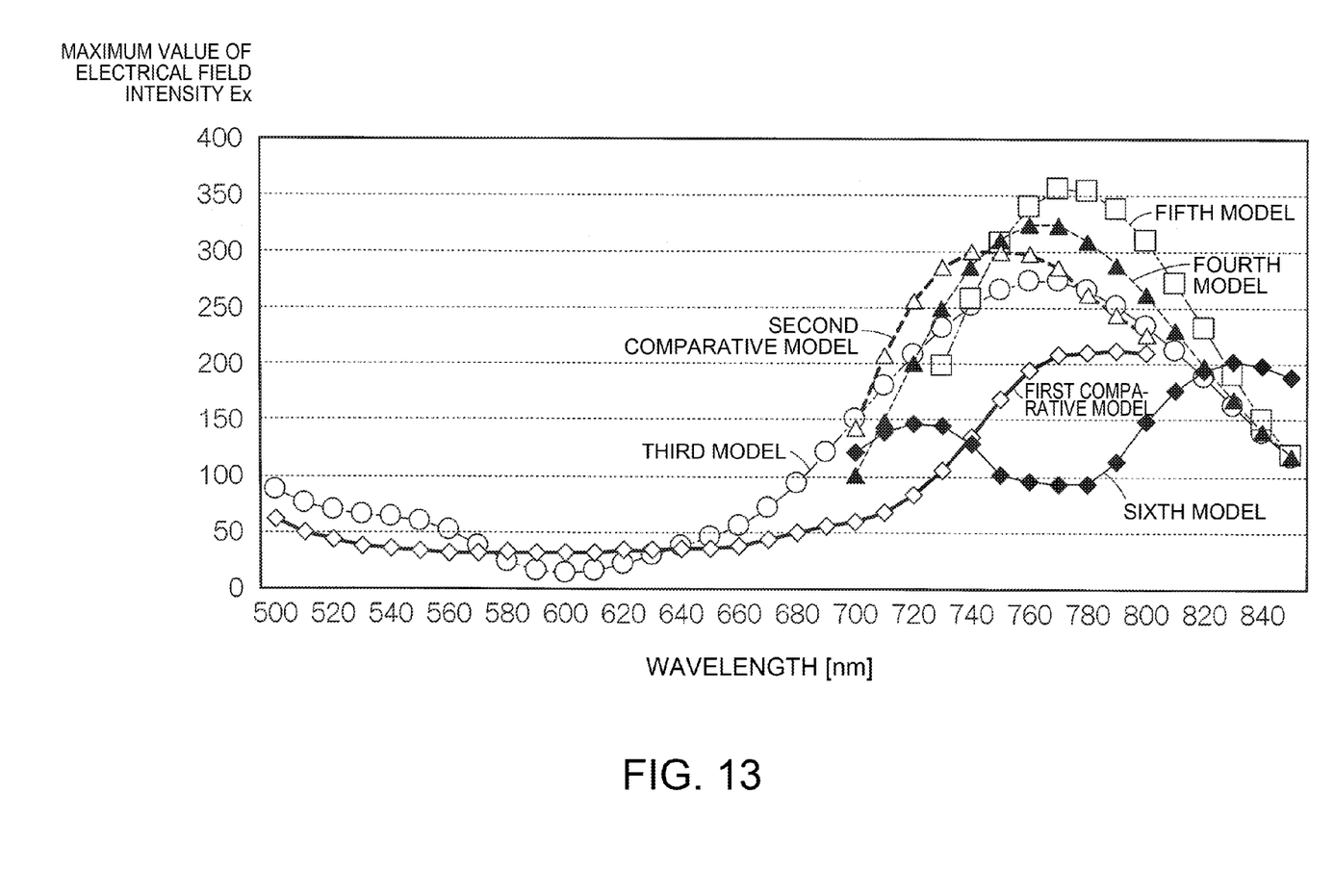
FIG. 13 is a graph showing a wavelength dependency of the maximum value of the electrical field intensity in the third model, the fifth model, and the first and second comparative models model by model.

FIG. 13 similarly shows a wavelength dependency of the electrical field intensity Ex. Here, the maximum value of the electrical field intensity Ex was identified. In calculating the maximum value, the third through sixth models, the first comparative model, and the second comparative model were used. As is obvious from FIG. 13, in the third through fifth models, larger maximum values compared to the first comparative model were observed in accordance with the formation of the metal nano-projection lines 16. In particular, in the fourth model and the fifth model, larger maximum values than in the first comparative model and the second comparative model were observed. On this occasion, it is observed that in the fourth model and the fifth model, the surface density of the metal nano-projections 15 is higher compared to the second comparative model. As is obvious from FIGS. 8 and 9, the long pitch LP of each of the fourth model and the fifth model corresponds to a dimension for establishing a first-order minimum of the reflectance at a wavelength shorter than the resonance wavelength of the localized surface plasmon resonance generated in the metal nano-projections 15 and further establishing higher-order minimums than the first order at a wavelength longer than the resonance wavelength of the localized surface plasmon resonance.

(3) Manufacturing Method of Sample Analysis Element

The sample analysis element 11 can be manufactured using a known manufacturing method. Specifically, in the manufacture of the sample analysis element 11, a glass wafer is prepared. On the surface of the glass wafer, there are stacked a gold film and a silicon dioxide film in sequence. In stacking, it is sufficient to use, for example, a plating process or a sputtering process. A stacked film is formed on the entire surface of the silicon dioxide film with the material of the metal nano-projections 15. On the surface of the stacked film, there is formed a mask modeled on the metal nano-projections 15. It is sufficient to use, for example, a photoresist for the mask. When the stacked film is removed in the periphery of the mask, the individual metal nano-projections 15 are formed from the stacked film. In such formation, it is sufficient to perform an etching process and a milling process. The individual substrate 12 is carved out from the glass wafer.

(4) Detection Device According to Embodiment

Figure 14:
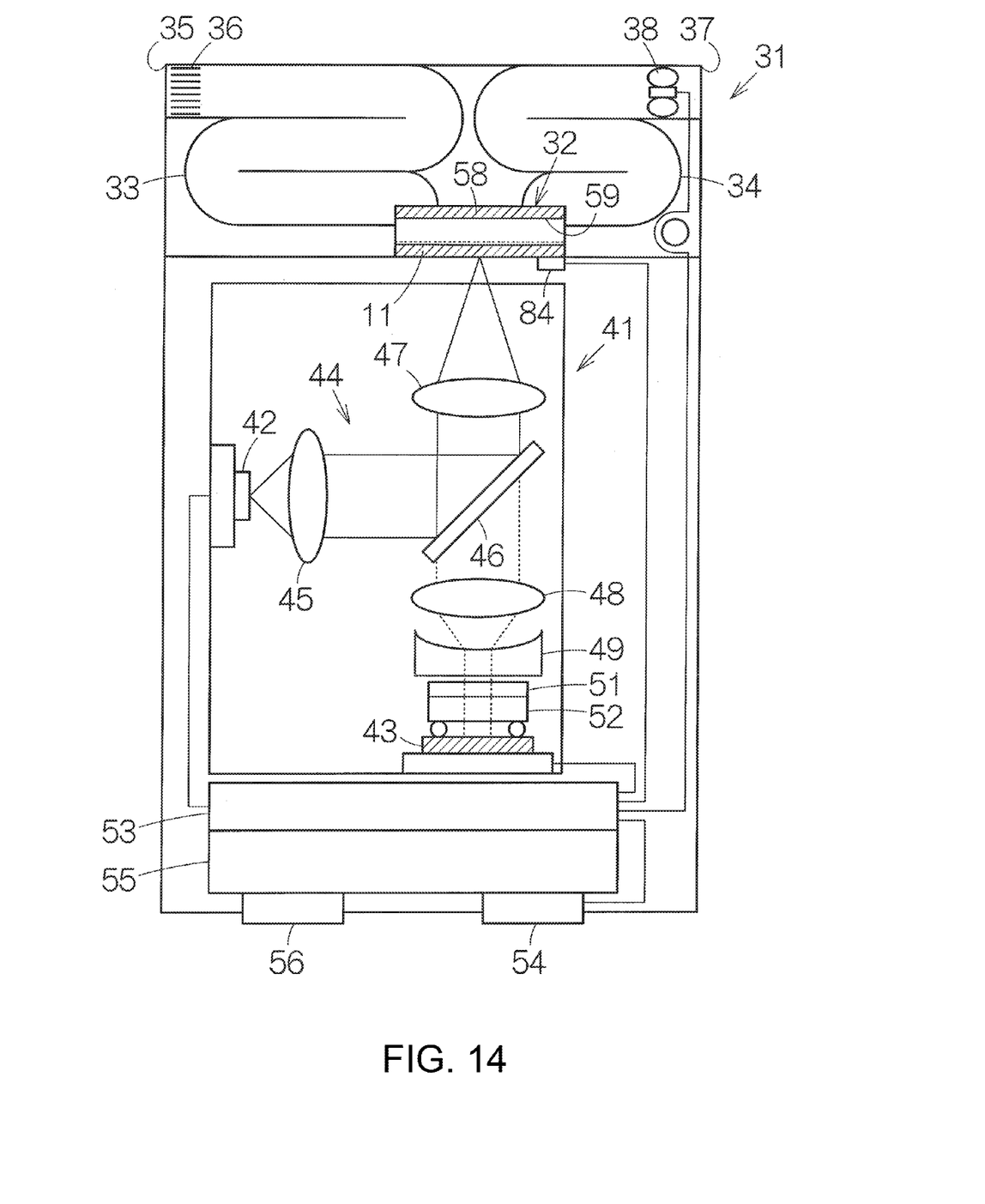
FIG. 14 is a conceptual diagram schematically showing a configuration of a target molecule detection device.

FIG. 14 schematically shows a target molecule detection device (detection device) 31 according to an embodiment. The target molecule detection device 31 is provided with a sensor unit 32. To the sensor unit 32, an introductory passage 33 and a discharge passage 34 are individually connected. A gas is introduced from the introductory passage 33 to the sensor unit 32. The gas is discharged from the sensor unit 32 to the discharge passage 34. A filter 36 is disposed in a passage entrance 35 of the introductory passage 33. The filter 36 can remove, for example, dust and moisture in the gas. A suction unit 38 is disposed in a passage exit 37 of the discharge passage 34. The suction unit 38 is formed of a blast fan. In accordance with the action of the blast fan, the gas flows through the introductory passage 33, the sensor unit 32, and the discharge passage 34 in sequence. In such a flow channel of the gas, shutters (not shown) are disposed at anterior and posterior positions of the sensor unit 32. In accordance with the open-close operation of the shutters, the gas can be confined in the sensor unit 32.

The target molecule detection device 31 is provided with a Raman scattered light detection unit 41. The Raman scattered light detection unit 41 irradiates the sensor unit 32 with irradiation light to detect the Raman scattered light. The Raman scattered light detection unit 41 incorporates a light source 42. A laser source can be used for the light source 42. The laser source can radiate a laser beam, which is linearly polarized light, and has a specific wavelength (a single wavelength).

The Raman scattered light detection unit 41 is provided with a light receiving element 43. The light receiving element 43 can detect, for example, the intensity of the light. The light receiving element 43 can output a detection current in accordance with the intensity of the light. Therefore, the intensity of the light can be identified in accordance with the magnitude of the current output from the light receiving element 43.

An optical system 44 is built between the light source 42 and the sensor unit 32, and between the sensor unit 32 and the light receiving element 43. The optical system 44 forms an optical path between the light source 42 and the sensor unit 32, and at the same time, forms an optical path between the sensor unit 32 and the light receiving element 43. The light of the light source 42 is guided to the sensor unit 32 by action of the optical system 44. The reflected light of the sensor unit 32 is guided to the light receiving element 43 by action of the optical system 44.

The optical system 44 is provided with a collimator lens 45, a dichroic mirror 46, a field lens 47, a collecting lens 48, a concave lens 49, an optical filter 51, and a spectroscope 52. The dichroic mirror 46 is disposed, for example, between the sensor unit 32 and the light receiving element 43. The field lens 47 is disposed between the dichroic mirror 46 and the sensor unit 32. The field lens 47 collects the parallel light supplied from the dichroic mirror 46, and then guides it to the sensor unit 32. The reflected light of the sensor unit 32 is converted by the field lens 47 into parallel light, and is then transmitted through the dichroic mirror 46. Between the dichroic mirror 46 and the light receiving element 43, there are disposed the collecting lens 48, the concave lens 49, the optical filter 51, and the spectroscope 52. The optical axes of the field lens 47, the collecting lens 48, and concave lens 49 are concentrically adjusted. The light collected by the collecting lens 48 is converted again into parallel light by the concave lens 49. The optical filter 51 removes the Rayleigh scattered light. The Raman scattered light passes through the optical filter 51. The spectroscope 52 selectively transmits, for example, the light with a specific wavelength. In such a manner as described above, in the light receiving element 43, the intensity of the light is detected at each of the specific wavelengths. An etalon, for example, can be used for the spectroscope 52.

The optical axis of the light source 42 is perpendicular to the optical axes of the field lens 47 and the collecting lens 48. The surface of the dichroic mirror 46 intersects with these optical axes at an angle of 45 degrees. Between the dichroic mirror 46 and the light source 42, there is disposed the collimator lens 45. In such a manner as described above, the collimator lens 45 is made to face the light source 42. The optical axis of the collimator lens 45 is adjusted to be coaxial with the optical axis of the light source 42.

The target molecule detection device 31 is provided with a control unit 53. To the control unit 53, there are connected the light source 42, the spectroscope 52, the light receiving element 43, the suction unit 38, and other equipment. The control unit 53 controls the operations of the light source 42, the spectroscope 52, and the suction unit 38, and at the same time, processes the output signal of the light receiving element 43. To the control unit 53, there is connected a signal connector 54. The control unit 53 can exchange signals with the outside through the signal connector 54.

The target molecule detection device 31 is provided with a power supply unit 55. The power supply unit 55 is connected to the control unit 53. The power supply unit 55 supplies the control unit 53 with operating power. The control unit 53 can operate with the power supplied from the power supply unit 55. For example, a primary battery and a secondary battery can be used for the power supply unit 55. The secondary battery can include, for example, a power supply connector 56 for recharging.

The control unit 53 is provided with a signal processing control section. The signal processing control section can be formed of, for example, a central processing unit (CPU), and a storage circuit such as a random access memory (RAM) or a read-only memory (ROM). In the ROM, there can be stored, for example, a processing program and spectrum data. The spectrum of the Raman scattered light of the target molecule is identified with the spectrum data. The CPU executes the processing program while temporarily taking the processing program and the spectrum data in the RAM. The CPU compares the spectrum of the light identified by action of the spectroscope and the light receiving element with the spectrum data.

The sensor unit 32 is provided with a sensor chip 11. The sensor chip 11 is made to face a substrate 58. Between the sensor chip 11 and the substrate 58, there is formed a gas chamber 59. The gas chamber 59 is connected to the introductory passage 33 at an end, and is connected to the discharge passage 34 at the other end. The metal nano-projections 15 are disposed inside the gas chamber 59. The light emitted from the light source 42 is converted by the collimator lens 45 into the parallel light. The light of the linear polarized light is reflected by the dichroic mirror 46. The light thus reflected is collected by the field lens 47, and the sensor unit 32 is irradiated with the light thus collected. On this occasion, the light can be input in a vertical direction perpendicular to the surface of the sensor chip 11. So-called normal incidence can be established. The polarization plane of the light is adjusted to be parallel to a protruded bar 14. The localized surface plasmon resonance is caused in the metal nano-projections 15 by action of the light irradiated. The near-field light is enhanced between the metal nano-projections 15. So-called hot spots are formed.

On this occasion, if the target molecules adhere to the metal nano-projections 15 at the hot spots, the Rayleigh scattered light and the Raman scattered light are generated from the target molecules. So-called surface-enhanced Raman scattering is realized. As a result, the light is emitted toward the field lens 47 with the spectrum corresponding to the type of the target molecule.

In such a manner as described above, the light emitted from the sensor unit 32 is converted by the field lens 47 into the parallel light, and then passes through the dichroic mirror 46, the collecting lens 48, the concave lens 49, and the optical filter 51. The Raman scattered light enters the spectroscope 52. The spectroscope 52 disperses the Raman scattered light. In such a manner as described above, the light receiving element 43 detects the intensity of the light at each of the specific wavelengths. The spectrum of the light is compared with the spectrum data. The target molecule can be detected in accordance with the spectrum of the light. In such a manner as described above, the target molecule detection device 31 can detect the target substance such as adenovirus, rhinovirus, HIV virus, or flu virus based on the surface-enhanced Raman scattering.

It should be noted that although the present embodiment is hereinabove explained in detail, it should easily be understood by those skilled in the art that it is possible to make a variety of modifications not substantially departing from the novel matters and the advantages of the invention. Therefore, such modified examples are all included in the scope of the invention. For example, a term described at least once with a different term having a broader sense or the same meaning in the specification or the accompanying drawings can be replaced with the different term in any part of the specification or the accompanying drawings. Further, the configurations and the operations of the sample analysis element 11, the target molecule detection device 31, and so on are not limited to those explained in the present embodiment, but can variously be modified.

The invention claimed is:

1. A sample analysis element comprising:
a plurality of metal nanobody lines disposed on a dielectric surface, each of the metal nanobody lines including a plurality of metal nanobodies arranged in a line at a first pitch smaller than a wavelength of incident light,
and the metal nanobody lines are arranged in parallel to each other at a second pitch larger than the first pitch;
wherein the second pitch is set to a dimension for establishing a first-order minimum of reflectance at a wavelength shorter than a resonance wavelength of a localized surface plasmon resonance generated in the metal nanobodies, and further establishing a higher-order minimum than the first-order at a wavelength longer than the resonance wavelength of the localized resonance plasmon resonance.

2. The sample analysis element according to claim 1, wherein
a region including no metal nanobody is formed between the metal nanobody lines.

3. The sample analysis element according to claim 2, further comprising:
a metal film; and
a dielectric body extending on a surface of the metal film to form the dielectric surface.

4. A detection device comprising:
the sample analysis element according to claim 3;
a light source adapted to emit light toward the metal nanobody lines; and
a light detector adapted to detect light emitted from the metal nanobody lines in accordance with irradiation with the light.

5. A detection device comprising:
the sample analysis element according to claim 3;
a light source adapted to emit light toward the metal nanobody lines; and
a light detector adapted to detect light emitted from the metal nanobody lines in accordance with irradiation with the light.

6. A detection device comprising:
the sample analysis element according to claim 2;
a light source adapted to emit light toward the metal nanobody lines; and
a light detector adapted to detect light emitted from the metal nanobody lines in accordance with irradiation with the light.

7. A detection device comprising:
the sample analysis element according to claim 1;
a light source adapted to emit light toward the metal nanobody lines; and
a light detector adapted to detect light emitted from the metal nanobody lines in accordance with irradiation with the light.

* * * * *